(12) United States Patent
Ishizaki

(10) Patent No.: US 11,396,104 B2
(45) Date of Patent: Jul. 26, 2022

(54) ARTIFICIAL EPIDERMIS STRUCTURE

(71) Applicant: Honda Motor Co., Ltd., Tokyo (JP)

(72) Inventor: Ryusuke Ishizaki, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 227 days.

(21) Appl. No.: 16/784,258

(22) Filed: Feb. 7, 2020

(65) Prior Publication Data

US 2020/0269440 A1     Aug. 27, 2020

(30) Foreign Application Priority Data

Feb. 22, 2019  (JP) .............................. JP2019-030437

(51) Int. Cl.
*B25J 15/00*     (2006.01)
(52) U.S. Cl.
CPC ....... *B25J 15/0038* (2013.01); *B25J 15/0023* (2013.01)
(58) Field of Classification Search
CPC ........................... B25J 15/0023; B25J 15/0038
See application file for complete search history.

(56) References Cited

U.S. PATENT DOCUMENTS

| | | | |
|---|---|---|---|
| 2016/0331556 A1* | 11/2016 | Wij | A42B 3/122 |
| 2019/0217487 A1* | 7/2019 | Takahashi | B25J 15/0616 |
| 2020/0215701 A1* | 7/2020 | Takahashi | B25J 15/0616 |
| 2020/0215702 A1* | 7/2020 | Takahashi | B25J 15/12 |

FOREIGN PATENT DOCUMENTS

| | | |
|---|---|---|
| JP | 2004217424 | 8/2004 |
| JP | 2004230041 | 8/2004 |
| JP | 2004230532 | 8/2004 |
| JP | 2004337307 | 12/2004 |
| JP | 2007301168 | 11/2007 |
| JP | 2018130772 | 8/2018 |
| JP | 2019042845 | 3/2019 |
| WO | WO-2020165648 A1 * | 8/2020 ........... B25J 15/0023 |

OTHER PUBLICATIONS

"Office Action of Japan Counterpart Application", dated Sep. 29, 2020, with English translation thereof, p. 1-p. 4.

* cited by examiner

*Primary Examiner* — Saul Rodriguez
*Assistant Examiner* — Brendan P Tighe
(74) *Attorney, Agent, or Firm* — JCIPRNET

(57) ABSTRACT

An artificial epidermis structure capable of using a gel substance to adjust a frictional property with high precision is provided. When a front surface of a lid member comes into contact with a target object and pressure acts on the lid member, a part of the gel substance can escape into a space that is formed by concave portions on a front surface of a gel substance. Therefore, reduction in a repulsion force of the gel substance is achieved. Accordingly, the pressure can be appropriately transmitted to the gel substance via the lid member, and convex portions of the gel substance can be caused to easily bulge out over the front surface of the lid member via holes of the lid member.

2 Claims, 4 Drawing Sheets

ARTIFICIAL EPIDERMIS STRUCTURE

CROSS-REFERENCE TO RELATED APPLICATION

This application claims the priority benefit of Japan Application No. 2019-030437, filed on Feb. 22, 2019. The entirety of the above-mentioned patent application is hereby incorporated by reference herein and made a part of this specification.

BACKGROUND OF THE DISCLOSURE

Technical Field

The disclosure relates to an artificial epidermis structure used as an epidermis of a robot hand or the like.

Related Art

An artificial epidermis structure (artificial skin) is proposed which has a frictional property close to the frictional property of human skin and in which a weak frictional force can be applied to a target object when pressure received from the target object is small while a strong frictional force can be applied to the target object when the pressure is large (for example, see patent literature 1).

As the artificial epidermis structure in which the frictional property changes corresponding to pressure received from the target object, the following artificial epidermis structure is considered which has a configuration in which a gel substance is filled in a container equipped with a lid member having holes and the gel substance is caused to bulge out over a front surface of the lid member via the holes corresponding to an external force acting on the lid member.

However, when a repulsion force acting from the gel substance on the lid member becomes excessive, it is difficult to transmit the external force to the gel substance via the lid member, the bulge amount of the gel substance from the holes of the lid member is insufficient, and there is a high possibility that a desired frictional property cannot be realized.

LITERATURE OF RELATED ART

Patent Literature

[Patent literature 1] Japanese Patent Laid-Open No. 2004-230041

SUMMARY

The disclosure provides an artificial epidermis structure capable of using a gel substance to adjust a frictional property with high precision.

The artificial epidermis structure of a first aspect of the disclosure includes a container having an opening portion, a gel substance filled in the container, and a lid member having holes and disposed in the opening portion of the container so as to come into contact with the gel substance; the gel substance is caused to bulge out from the holes over a front surface of the lid member when pressure acts on the lid member; and concave portions being hollowed are formed on a part of at least one of a front surface of the gel substance and a back surface of the lid member so that a space to which the gel substance escapes is formed between the front surface of the gel substance and the back surface of the lid member.

According to the artificial epidermis structure having this configuration, when the front surface of the lid member comes into contact with a target object and pressure acts on the lid member, the gel substance can escape into the space that is formed by the concave portions on at least one of the front surface of the gel substance and the back surface of the lid member. Therefore, reduction in a repulsion force of the gel substance is achieved, and thereby the pressure can be appropriately transmitted to the gel substance via the lid member, and the gel substance can be caused to easily bulge out over the front surface of the lid member via the holes of the lid member. Then, the frictional force can be applied to the target object while the frictional property of the artificial epidermis structure determined only by the front surface of the lid member and the frictional property of the artificial epidermis structure determined by the front surface of the gel substance and the front surface of the lid member can be switched with high precision.

The artificial epidermis structure of a second aspect of the disclosure includes a plurality of artificial epidermis elements, wherein each of the plurality of artificial epidermis elements includes a container having an opening portion, a gel substance filled in the container, and a lid member having holes and disposed in the opening portion of the container so as to come into contact with the gel substance; the gel substance is caused to bulge out from the holes over a front surface of the lid member when pressure acts on the lid member; concave portions being hollowed are formed in a part of at least one of a front surface of the gel substance and a back surface of the lid member so that a space to which the gel substance escapes is formed between the front surface of the gel substance and the back surface of the lid member; and at least one artificial epidermis element of the plurality of artificial epidermis elements is different from the other artificial epidermis elements in terms of at least one of the hole diameter of the lid member and the volume of the space.

According to the artificial epidermis structure having this configuration, since a plurality of artificial epidermis structures of the first aspect is included as the plurality of artificial epidermis elements, as described above, the frictional force can be applied to the target object while the frictional property of the artificial epidermis structure determined only by the front surface of the lid member and the frictional property of the artificial epidermis structure determined by the front surface of the gel substance and the front surface of the lid member can be switched with high precision.

In addition, at least one of the hole diameter of the lid member and the volume of the escape space of the gel substance is differentiated among the plurality of artificial epidermis elements. If the hole diameter is larger and the volume of the escape space is larger, the gel substance can bulge out over the front surface of the lid member under smaller pressure. Therefore, the frictional property of the artificial epidermis structure can be changed in steps corresponding to the change in the pressure that the artificial epidermis structure receives from the target object. For example, in a process in which the pressure increases, after the frictional property of the artificial epidermis structure determined by the front surface of the gel substance and the front surface of the lid member is realized in one artificial epidermis element or a plurality of artificial epidermis elements constituting a first artificial epidermis element group, the frictional property of the artificial epidermis structure determined by the front surface of the gel substance and the front surface of the lid member can be further realized in one artificial epidermis element or a plurality of artificial epidermis elements constituting a second artificial epidermis element group. Accordingly, from the artificial skin structure, the range expansion of variation aspects of the frictional force acting on the target object can be achieved.

DESCRIPTION OF THE EMBODIMENTS

First Embodiment (Configuration)

Figure 1:
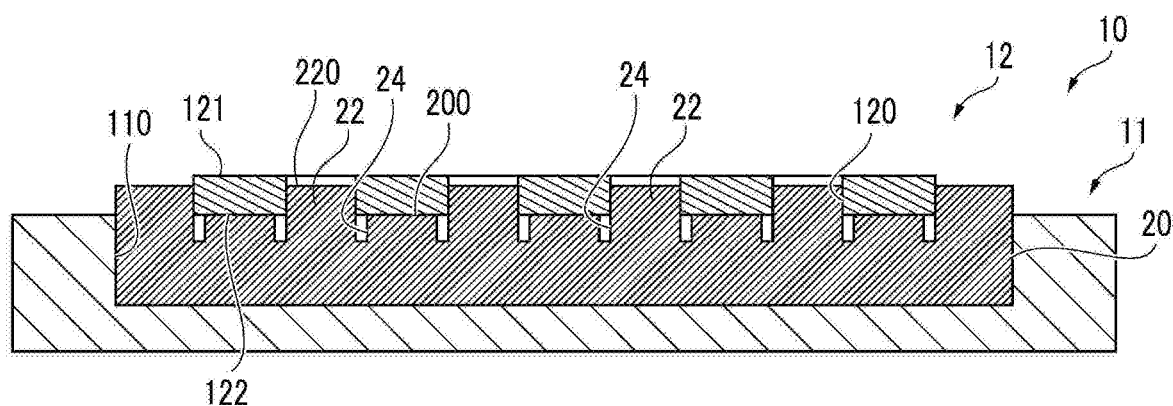
FIG. 1 is a schematic illustration diagram of a configuration of an artificial epidermis structure used as a first embodiment of the disclosure.

An artificial epidermis structure used as a first embodiment of the disclosure shown in FIG. 1 includes a container with lid 10 and a gel substance 20 accommodated in the container with lid 10. FIG. 1 is a schematic diagram, and an aspect ratio or the like of each of the container with lid 10, the gel substance 20, and each component thereof is different from an actual artificial epidermis structure (the same also applies to FIG. 2 and the following diagrams).

The container with lid 10 includes a container 11 and a lid member 12. The container 11 is configured by a substantially disc-shaped synthetic resin for example, and has a concave portion 110 in which a central portion is concave in a substantially cylindrical shape from an upper end surface of the container 11. In the lid member 12, a plurality of holes 120 is formed. The plurality of holes 120 has a diameter slightly smaller than that of the concave portion 110 of the container 10, is configured by, for example, a substantially disc-shaped synthetic resin or rubber such as silicone rubber or the like, and extends in a thickness direction from a front surface 121 to a back surface 122 of the lid member 12.

Figure 2:
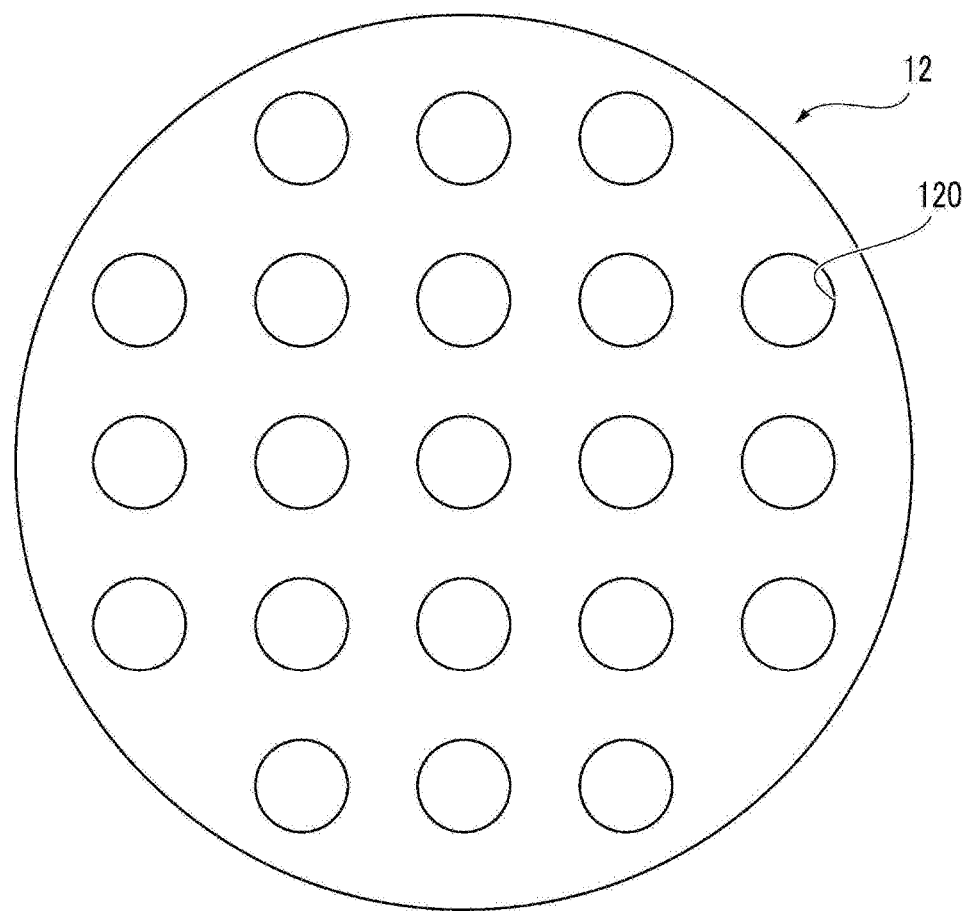
FIG. 2 is a top view of a container and a gel substance filled in the container.

For example, as shown in FIG. 2, the lid member 12 has a total of 21 holes 120 having a substantially circular shape in a top view as the plurality of holes 120, the plurality of holes 120 being spaced apart to form lattice points of a square lattice. The plurality of holes 120 may not be the same in diameter. The number of the holes 120 may be one or a plural number other than 21. The plurality of holes 120 may be disposed in various forms. For example, the plurality of holes 120 may be disposed to form lattice points of a triangular lattice, or may be discretely disposed in a peripheral direction of each concentric circle. The top-view shape of the hole 21 may be various shapes such as an elliptical shape, a triangular shape, a rectangular shape, a polygonal shape and the like in addition to the circular shape.

The gel substance 20 is configured by a flexible urethane resin for example. The gel substance 20 is formed into a substantially disc shape having a diameter slightly smaller than that of the concave portion 110 of the container 11 and is accommodated in the concave portion 110 and covered by the lid member 12, and thereby the back surface 122 of the lid member 12 is in contact with a front surface 200 of the gel substance 20.

The gel substance 20 has a concave-convex structure on the front surface 200 thereof. Specifically, the gel substance 20 has a plurality of convex portions 22 that protrudes more than the front surface 200 at points corresponding to the plurality of holes 120 of the lid member 12. Each of the plurality of convex portions 22 has a substantially frusto-conical lower portion and a substantially cylindrical upper portion that uses the upper bottom surface of the lower portion as a bottom surface and has a diameter slightly smaller than that of the holes 120 so as to fit the shape of the holes 120 of the lid member 12. In a state that the pressure or external force does not acts on the lid member 12, an end surface 220 of each convex portion 22 is drawn back from the front surface 121 of the lid member 12 and is present in each hole 120. Each convex portion 22 has various shapes according to the shape of the holes 120 of the lid member 12, such as a substantially truncated pyramid shape, a substantially rectangular column shape or the like in addition to the substantially frusto-conical shape or the substantially cylindrical shape.

Figure 3:
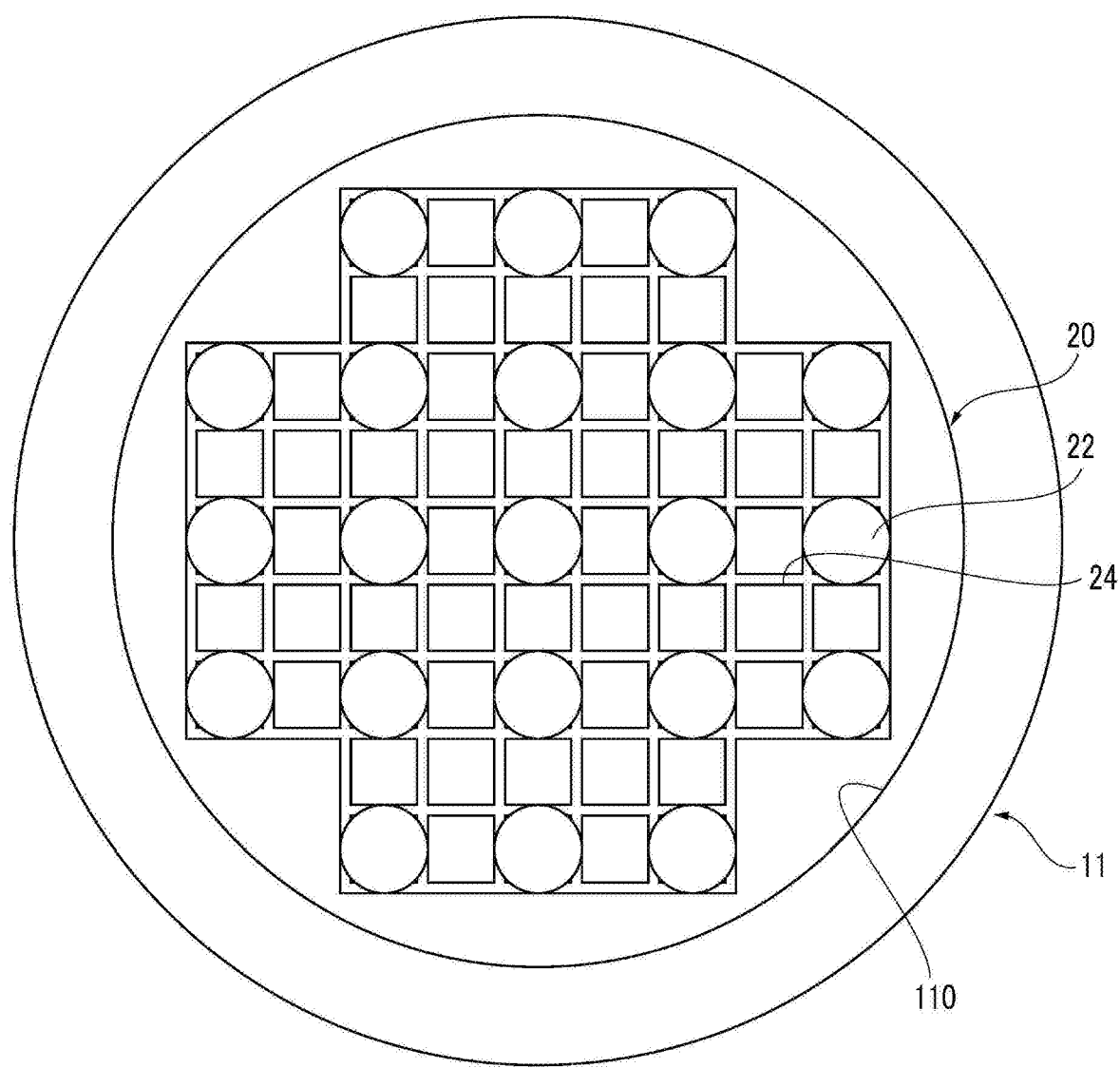
FIG. 3 is a top view of a lid member.

The gel substance 20 has concave portions 24 that are more concave than the front surface 200 around each convex portion 22. The plurality of concave portions 24 is formed, corresponding to the arrangement forms of the plurality of holes 120 of the lid member 12, on the gel substance 20 along a plurality of straight line segments intersecting and extending vertically and horizontally around the plurality of (a total of 21) convex portions 22 that is disposed to form lattice points of a square lattice as shown in FIG. 3 for example.

The concave portions 24 may extend to continuously enclose each convex portion 22 over the entire periphery, or may extend to intermittently enclose at least some convex portions 22 over the entire periphery or partially continuously or intermittently enclose at least some convex portions 22 within the entire periphery. The shape of the concave portions 24 on a cross section including a central axis of the gel substance 20 may be various shapes such as a substantially semi-circular shape, a substantially semi-elliptical shape, a substantially rectangular shape or the like in addition to the substantially trapezoidal shape.

(Function)

Figure 4:
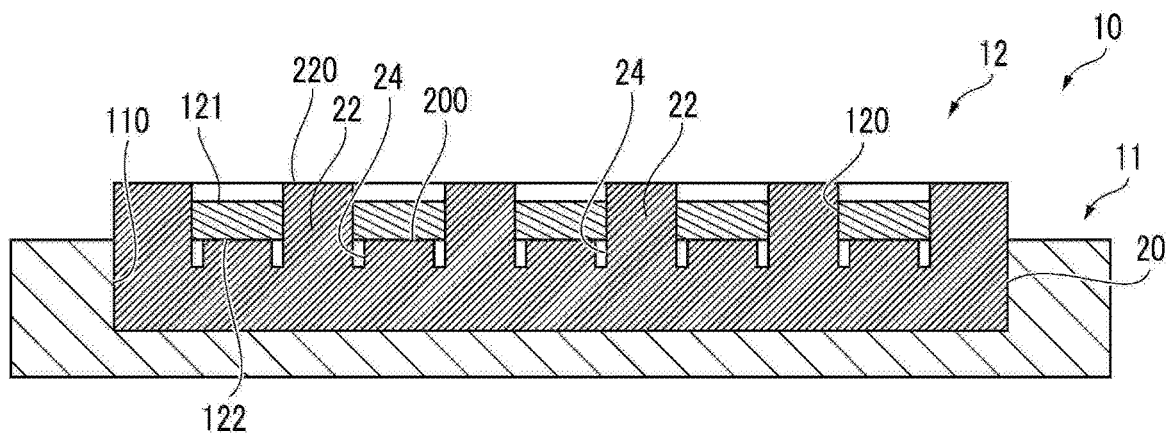
FIG. 4 is an illustration diagram related to a function of the artificial epidermis structure used as the first embodiment of the disclosure.

According to the artificial epidermis structure having this configuration, when the front surface 121 of the lid member 12 comes into contact with the target object and pressure acts on the lid member 12, a part of the gel substance 20 can escape into the space formed by the concave portions 24 on the front surface 200 of the gel substance 20. Therefore, reduction in a repulsion force of the gel substance 20 is achieved. Accordingly, the pressure can be appropriately transmitted to the gel substance 20 via the lid member 12, and as shown in FIG. 4, the convex portions 22 of the gel substance 20 can be caused to easily bulge out over the front surface 121 of the lid member 120 via the holes 120 of the lid member 12. Then, the frictional force can be applied to the target object while the frictional property (see FIG. 1) of the artificial epidermis structure determined only by the front surface 121 of the lid member 12 and the frictional property (see FIG. 4) of the artificial epidermis structure determined by the end surface 220 of the convex portions 22 of the gel substance 20 and the front surface 121 of the lid member 12 can be switched with high precision.

EXAMPLE

Example 1-1

A substantially disc-shaped container 11 having a diameter ϕ of 58 mm and a thickness t of 15 mm is prepared, and the container 11 has a concave portion 110 concave into a substantially cylindrical shape having a diameter ϕ of 50 mm and a depth d of 5 mm. A substantially disc-shaped lid member 12 having a diameter ϕ of 48 mm and a thickness t of 2.5 mm is prepared in which a total of 37 (=1×3+1×5+3×7+1×5+1×3) holes 120 having a diameter ϕ of 3 mm and disposed to form lattice points of a substantially square lattice. A substantially disc-shaped polyurethane gel having a diameter ϕ of 48 mm, a thickness t of 3 mm and an ASKER C hardness of "0" is prepared as the gel substance 20. On the front surface 200 of the gel substance 20, a total of 37 substantially frusto-conical convex portions 22 disposed to form lattice points of a square lattice and the concave portions 24 are formed, the convex portions 22 having a substantially trapezoidal cross section in which the lower width is 3 mm, the upper width is 2.302 mm, and the height is 3.5 mm, the concave portions 24 extending vertically and horizontally around each convex portion 22 and having a substantially trapezoidal cross section in which the lower width is 3.4 mm, the upper width is 3 mm, and the height is 2 mm. The volume of a space that is formed by the concave portions 24 between the lid member 12 and the gel substance 20 is 2211.367 mm³. By the container 11, the lid member 12, and the gel substance 20, the artificial epidermis structure of Example 1-1 is manufactured.

Example 1-2

The artificial epidermis structure of Example 1-2 having the same configuration as Example 1-1 except that a polyurethane gel having an ASKER C hardness of "7" is prepared as the gel substance 20 is manufactured.

Example 2-1

A substantially disc-shaped lid member 12 having a diameter ϕ of 4 mm and a thickness t of 2.5 mm is prepared, and a total of 21 (=1×3+3×5+1×3) holes 120 having a diameter ϕ of 4 mm and disposed to form lattice points of a substantially square lattice are formed in the lid member 12 (see FIG. 2). On the front surface 200 of the gel substance 20, a total of 21 substantially frusto-conical convex portions 22 disposed to form lattice points of a square lattice and the concave portions 24 are formed, the convex portions 22 having a substantially trapezoidal cross section in which the lower width is 4 mm, the upper width is 3.302 mm, and the height is 3.5 mm, the concave portions 24 extending vertically and horizontally around each convex portion 22 (see FIG. 3). The volume of the space that is formed by the concave portions 24 between the lid member 12 and the gel substance 20 is 2457.982 mm³. The artificial epidermis structure of Example 2-1 having the same configuration as Example 1-1 except for the above configuration is manufactured.

Example 2-2

The artificial epidermis structure of Example 2-2 having the same configuration as Example 2-1 except that a polyurethane gel having an ASKER C hardness of "7" is prepared as the gel substance 20 is manufactured.

Example 3-1

A substantially disc-shaped lid member 12 having a diameter ϕ of 6 mm and a thickness t of 2.5 mm is prepared, and a total of 9 (=3×3) holes 120 having a diameter ϕ of 6 mm and disposed to form lattice points of a substantially square lattice are formed in the lid member 12. On the front surface 200 of the gel substance 20, a total of 9 substantially frusto-conical convex portions 22 disposed to form lattice points of a square lattice and the concave portions 24 are formed, the convex portions 22 having a substantially trapezoidal cross section in which the lower width is 6 mm, the upper width is 5.302 mm, and the height is 3.5 mm, the concave portions 24 extending vertically and horizontally around each convex portion 22. The volume of the space that is formed by the concave portions 24 between the lid member 12 and the gel substance 20 is 2642.708 mm³. The artificial epidermis structure of Example 3-1 having the same configuration as Example 1-1 except for the above configuration is manufactured.

Example 3-2

The artificial epidermis structure of Example 3-2 having the same configuration as Example 3-1 except that a polyurethane gel having an ASKER C hardness of "7" is prepared as the gel substance 20 is configured.

COMPARATIVE EXAMPLE

Artificial epidermis structures of Comparative example 1, Comparative example 2, and Comparative example 3 respectively having the same configuration as Example 1-1, Example 2-1, and Example 3-1 except that the concave portions 24 are omitted in the gel substance 20 (the space volume is about 0 mm³) are manufactured.

(Evaluation test)

Figure 5:
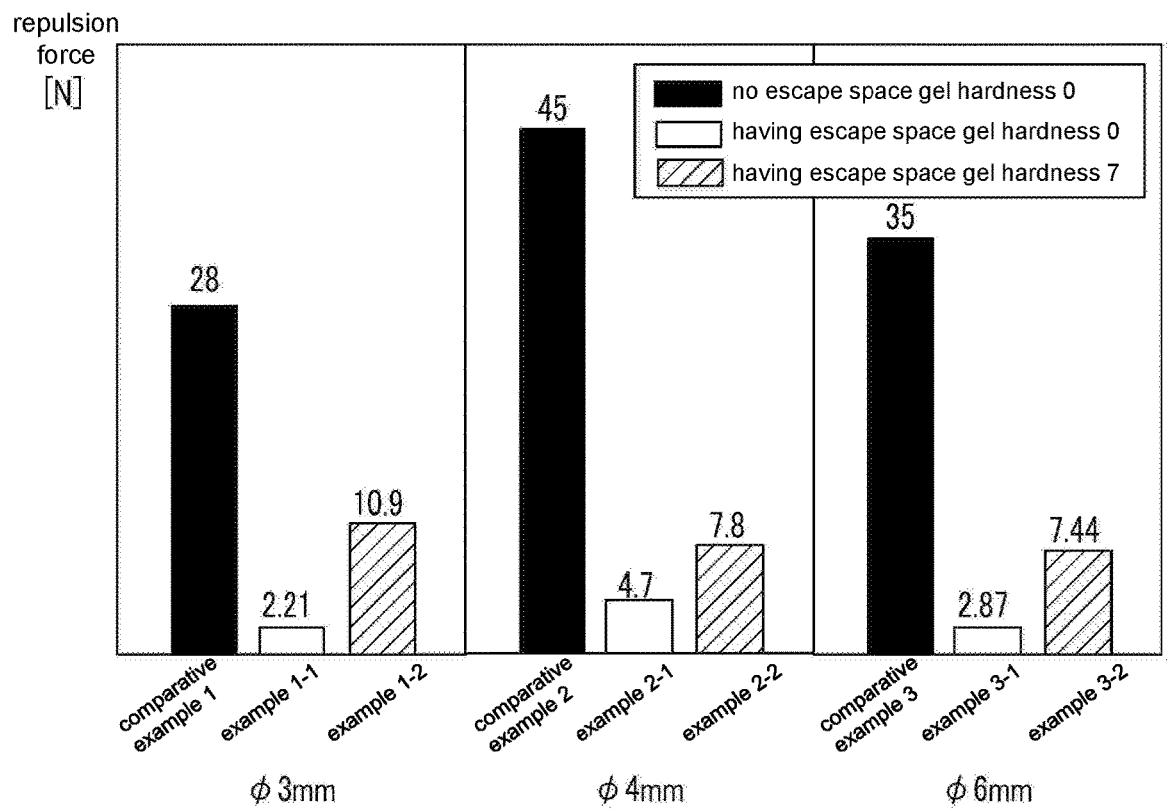
FIG. 5 is an illustration diagram related to a function of artificial epidermis structures of examples and comparative examples of the disclosure.

For the artificial epidermis structure of each example and each comparative example, a repulsion force of the gel substance 20 when the lid member 12 is pressed down by 1 mm is measured. The repulsion force is measured by a force gauge. The test result is shown in FIG. 5. As is clear from FIG. 5, by forming the concave portions 24 in the gel substance 20 and forming the space to which the gel substance 20 escapes between the lid member 12 and the gel substance 20 by the concave portions 24, each example is significantly reduced in repulsion force of the gel substance 20 compared with each comparative example.

Second Embodiment (Configuration)

Figure 6:
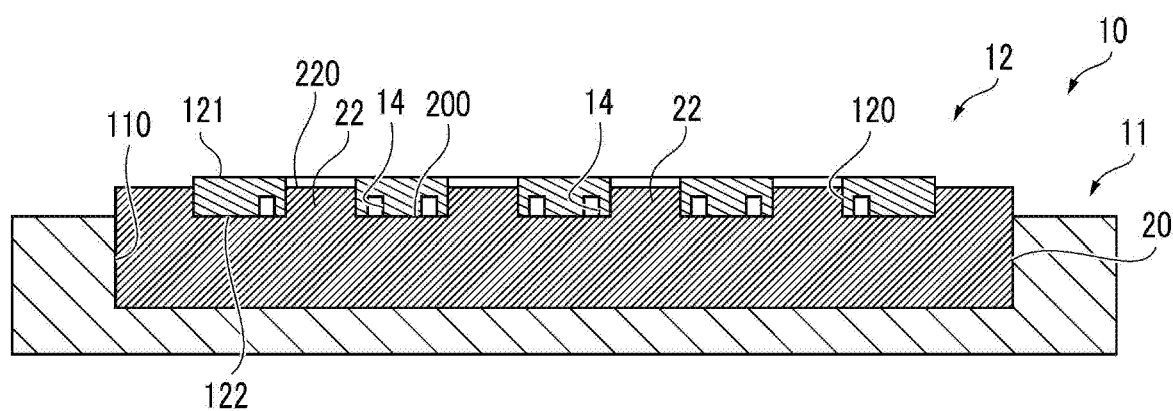
FIG. 6 is a schematic illustration diagram of a configuration of an artificial epidermis structure used as a second embodiment of the disclosure.

In an artificial epidermis structure used as a second embodiment of the disclosure shown in FIG. 6, instead of omitting the concave portions 24 in the gel substance 20, concave portions 14 which extend to enclose each hole 120 over the entire periphery or partially enclose each hole 120 continuously or intermittently and which are more concave than the back surface 122 are formed on the back surface 122 of the lid member 12. The other configurations are the same as the artificial epidermis structure of the first embodiment, and thus identical reference signs are used for the same configurations and the description is omitted.

(Function)

According to the artificial epidermis structure having this configuration, when the front surface 121 of the lid member 12 comes into contact with the target object and pressure acts on the lid member 12, a part of the gel substance 20 can escape into the space that is formed by the concave portions 14 on the back surface 122 of the lid member 12. Therefore, reduction in repulsion force of the gel substance 20 is achieved. Accordingly, the pressure can be appropriately transmitted to the gel substance 20 via the lid member 12, and the convex portions 22 of the gel substance 20 can be caused to easily bulge out over the front surface 121 of the lid member 12 via the holes 120 of the lid member 12. Then, the frictional force can be applied to the target object while the frictional property of the artificial epidermis structure determined only by the front surface 121 of the lid member 12 and the frictional property of the artificial epidermis structure determined by the end surface 220 of the convex portions 22 of the gel substance 20 and the front surface 121 of the lid member 12 can be switched with high precision.

Another Embodiment of the Disclosure

An artificial epidermis structure of another embodiment of the disclosure includes the artificial epidermis structures (see FIG. 1 and FIG. 6) in the above embodiments as a plurality of artificial epidermis elements. At least one artificial epidermis element of the plurality of artificial epidermis elements is different from the other artificial epidermis elements in terms of at least one of the diameter of the holes 120 of the lid member 12 and the volume of the spaces formed of the concave portions 14, 24.

If the diameter of the hole 120 is larger and the volume of the escape space is larger, the gel substance 20 can bulge out over the front surface 121 of the lid member 12 under smaller pressure. Therefore, the frictional property of the artificial epidermis structure can be changed in steps corresponding to the change in the pressure that the artificial epidermis structure receives from the target object. For example, in the process in which the pressure increases, after the frictional property of the artificial epidermis structure determined by the front surface (the end surface 220 of the convex portions 22) of the gel substance 20 and the front surface 121 of the lid member 12 is realized in one artificial epidermis element or a plurality of artificial epidermis elements constituting a first artificial epidermis element group, the frictional property of the artificial epidermis structure determined by the front surface (the end surface 220 of the convex portions 22) of the gel substance 20 and the front surface 121 of the lid member 12 can be further realized in one artificial epidermis element or a plurality of artificial epidermis elements constituting a second artificial epidermis element group. Accordingly, from the artificial skin structure, the range expansion of variation forms of the frictional force acting on the target object can be achieved.

What is claimed is:

1. An artificial epidermis structure, comprising a container having an opening portion, a gel substance filled in the container, and a lid member having holes and disposed in the opening portion of the container so as to come into contact with the gel substance, wherein
   the gel substance is caused to bulge out from the holes over a front surface of the lid member when pressure acts on the lid member, and
   concave portions being hollowed are formed in a part of at least one of a front surface of the gel substance and a back surface of the lid member without overlapping the holes along an axial direction of each of the holes, so that a space to which the gel substance escapes is formed between the front surface of the gel substance and the back surface of the lid member.

2. An artificial epidermis structure, comprising a plurality of artificial epidermis elements,
   wherein each of the plurality of artificial epidermis elements comprises a container having an opening portion, a gel substance filled in the container, and a lid member having holes and disposed in the opening portion of the container so as to come into contact with the gel substance;
   the gel substance is caused to bulge out from the holes over a front surface of the lid member when pressure acts on the lid member;
   concave portion being hollowed are formed in a part of at least one of a front surface of the gel substance and a back surface of the lid member without overlapping the holes along an axial direction of each of the holes, so that a space to which the gel substance escapes is formed between the front surface of the gel substance and the back surface of the lid member; and
   at least one artificial epidermis element of the plurality of artificial epidermis elements is different from the other artificial epidermis elements in terms of at least one of the hole diameter of the lid member and the volume of the space.

* * * * *